United States Patent
Datteri et al.

(10) Patent No.: US 12,033,295 B2
(45) Date of Patent: Jul. 9, 2024

(54) METHOD AND SYSTEM FOR NON-CONTACT PATIENT REGISTRATION IN IMAGE-GUIDED SURGERY

(71) Applicant: Medtronic Navigation, Inc., Louisville, CO (US)

(72) Inventors: Ryan D. Datteri, Denver, CO (US); Yvan Paitel, Louisville, CO (US); Kevin E. Mark, Hawthorn Woods, IL (US); Samantha Joanne Preston, Denver, CO (US); Andrew Summers, Denver, CO (US); Ganesh Saiprasad, Broomfield, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 96 days.

(21) Appl. No.: 17/654,438

(22) Filed: Mar. 11, 2022

(65) Prior Publication Data

US 2023/0074362 A1 Mar. 9, 2023

Related U.S. Application Data

(60) Provisional application No. 63/162,420, filed on Mar. 17, 2021.

(51) Int. Cl.
*G06T 19/20* (2011.01)
*A61B 34/20* (2016.01)
(Continued)

(52) U.S. Cl.
CPC .............. *G06T 19/20* (2013.01); *A61B 34/20* (2016.02); *G06T 7/75* (2017.01); *G06T 17/20* (2013.01);
(Continued)

(58) Field of Classification Search
CPC .... G06T 7/0014; G06T 2200/04; G16H 10/65
See application file for complete search history.

(56) References Cited

U.S. PATENT DOCUMENTS

| 9,901,407 B2 | 2/2018 | Breisacher et al. |
| 2018/0262743 A1* | 9/2018 | Casas .................... G06F 3/0304 |

(Continued)

FOREIGN PATENT DOCUMENTS

| WO | 2014122301 A1 | 8/2014 | |
| WO | WO-2014122301 A1 * | 8/2014 | ............. A61B 34/20 |

OTHER PUBLICATIONS

Sangkyun Shin et al, Markerless Registration for Intracerebral Hemorrhage Surgical System Using Weighted Interative Closest Point (ICP), Engineering In Medicine and Biology Society (EMBC), 2013 34th Annual International Conference of the IEEE, IEEE, Aug. 28, 2012 (Aug. 28, 2012), pp. 5306-5309, XP032464135, ISSN: 1557-I70X, DOI: 10.1109/EMBC.2012.6347192 abstract section II.A figures 1, 2.

(Continued)

*Primary Examiner* — Samantha (Yuehan) Wang
(74) *Attorney, Agent, or Firm* — Harness, Dickey & Pierce, P.L.C.

(57) ABSTRACT

Systems and methods used to perform touchless registration of images for surgical navigation are disclosed. In some embodiments, the systems include a 3-D scanning device to capture spatial data of a region of interest of a patient and a reference frame. A digital mesh model is generated from the spatial data. A reference frame model is registered with the digital mesh model. Anatomical features of the digital mesh model and a patient registration model are utilized to register the digital mesh model with the patient registration model. A position of a surgical instrument is tracked relative to the reference frame and the patient registration model.

22 Claims, 13 Drawing Sheets

(51) Int. Cl.
*G06T 7/73* (2017.01)
*G06T 17/20* (2006.01)
*G06T 19/00* (2011.01)
*G06V 10/25* (2022.01)
*G06V 40/16* (2022.01)
*A61B 34/10* (2016.01)
*A61B 90/00* (2016.01)

(52) U.S. Cl.
CPC ............ *G06T 19/003* (2013.01); *G06V 10/25* (2022.01); *G06V 40/165* (2022.01); *G06V 40/171* (2022.01); *A61B 2034/102* (2016.02); *A61B 2034/2065* (2016.02); *A61B 2090/364* (2016.02); *G06T 2200/04* (2013.01); *G06T 2200/08* (2013.01); *G06T 2207/10076* (2013.01); *G06T 2207/10081* (2013.01); *G06T 2207/10088* (2013.01); *G06T 2207/30201* (2013.01); *G06T 2210/41* (2013.01); *G06T 2219/2004* (2013.01)

(56) References Cited

U.S. PATENT DOCUMENTS

| | | |
|---|---|---|
| 2018/0333207 A1* | 11/2018 | Moctezuma De la Barrera ......... A61B 34/10 |
| 2019/0029561 A1 | 1/2019 | Kim et al. |
| 2020/0038112 A1 | 2/2020 | Amanatullah et al. |
| 2021/0088811 A1* | 3/2021 | Varady ................. G02C 13/005 |

OTHER PUBLICATIONS

International Preliminary Report on Patentability, Written Opinion of the International Searching Authority (EPO), corresponding to PCT/US2022/071149, dated Sep. 28, 2023 (11 pages).

* cited by examiner ns of the appended
METHOD AND SYSTEM FOR NON-CONTACT PATIENT REGISTRATION IN IMAGE-GUIDED SURGERY

RELATED APPLICATIONS

This application claims priority to U.S. Provisional Application No. 63/162,420 filed on Mar. 17, 2021 and titled "Method and System for Non-Contact Patient Registration in Image-Guided Surgery" which is hereby incorporated by reference in its entirety.

TECHNICAL FIELD

The present disclosure relates generally to systems and methods to surgically treat a patient. More specifically, the present disclosure relates to systems and methods used to track medical instruments within a surgical field relative to a pre-operative image. In some embodiments, the present disclosure relates to systems and methods used to register a spatially scanned image of a region of interest and reference frame with the pre-operative image.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1:
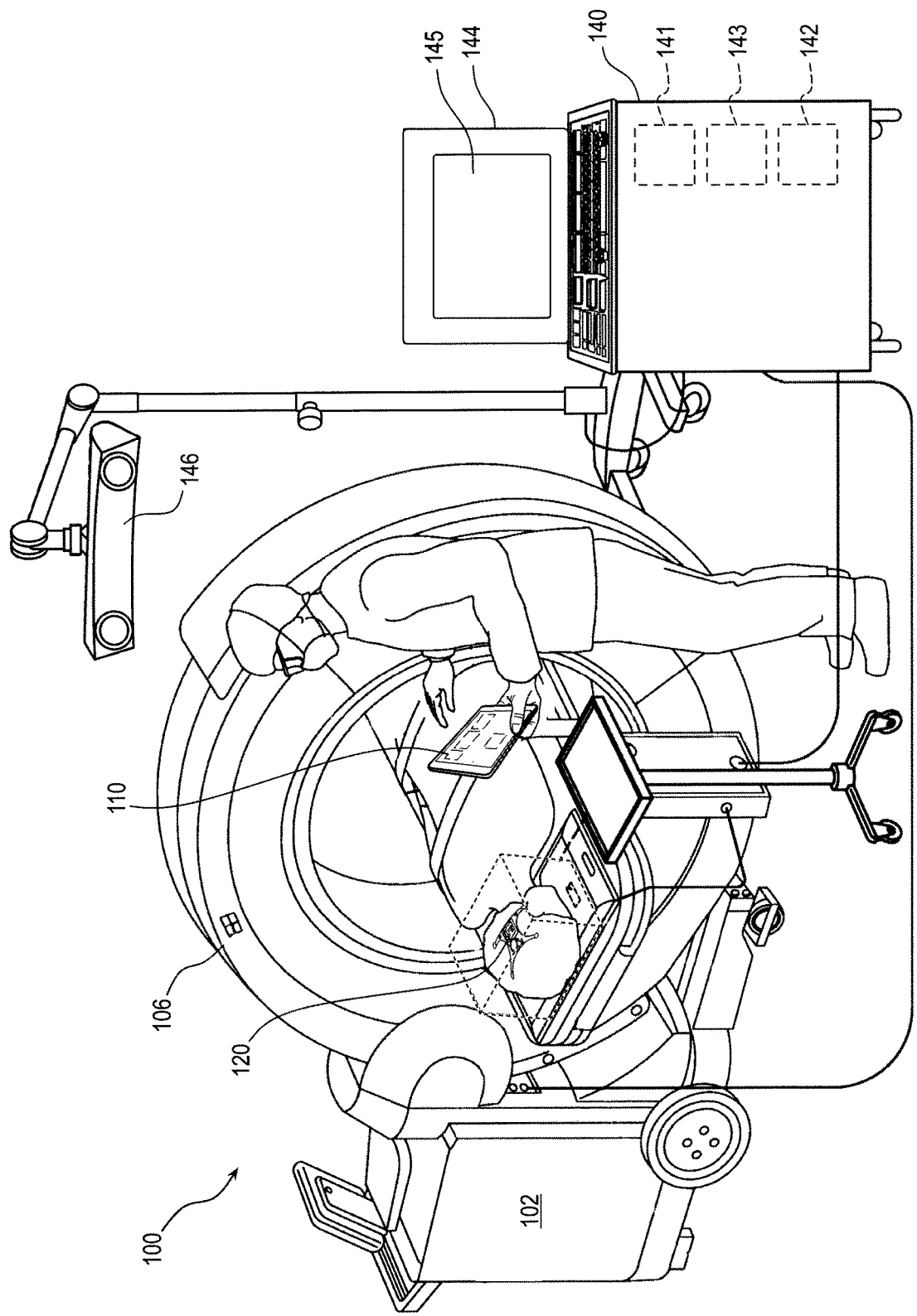
FIG. 1 is a schematic view of an embodiment of a non-contact patient registration system.

In certain instances, a patient may require surgical treatment of an area of his/her body that is not readily accessible to a clinician, such as the patient's brain. In these instances, diagnostic images or preoperative images of the treatment area region of interest (ROI) can be acquired prior to the surgical treatment. For example, the preoperative images may be magnetic resonance images (MRI) or images from a computed tomography (CT) scan, among other imaging modalities. Prior to initiation of the surgical treatment, a 3D digital model of the ROI may be generated. The 3D digital model can be registered to a navigation coordinate system to provide for electromagnetic (EM) or optical navigation during the surgical treatment.

Exemplary devices and methods within the scope of this disclosure relate to non-contact or touchless patient registration of a digital mesh model of an ROI and a reference frame with pre-operative images (including, e.g., a 3D model generated from the pre-operative images) to treat various regions of the body, including treatments within the brain, using EM or optical surgical navigation. Systems and methods within the scope of this disclosure include non-contact patient registration of the digital mesh model of the ROI and a reference frame with the pre-operative image of the patient. For example, non-contact patient registration systems within the scope of this disclosure may generate a digital mesh model of the patient's head and a reference frame and register the digital mesh model with a patient registration model or pre-operative image. Though specific examples relating to treatment of the brain are described herein, that disclosure can be analogously applied to treatment of other locations, such as the ear, nose, and throat; thoracic cavity; abdomen; and other areas.

In some embodiments within the scope of this disclosure, a non-contact patient registration system may comprise a 3-D scanning device, a reference frame, and a workstation. The 3-D scanning device can include a camera, a lens, a processor, a memory member, and a wireless communication device. The workstation can include a processor, a storage device (e.g., a non-transitory storage device), and a wireless communication device. In certain embodiments, the reference frame may include a structure configured to be coupled to a head holder. In other embodiments, the reference frame can include a two-dimensional bar code attachment and/or an EM tracking member.

In some treatments within the scope of this disclosure, the 3-D scanning device may be configured to spatially scan the ROI and the reference frame to capture spatial data and process the spatial data to generate a digital mesh model of the ROI and reference frame. The 3-D scanning device and/or the workstation can be configured to detect a position of the reference frame within the digital mesh model, register a registration model of the reference frame with a digital mesh model of the reference frame, detect anatomical features within the digital mesh model and a patient registration model, register the digital mesh model with the patient registration model using the detected anatomical features, track a position of a surgical instrument relative to the reference frame, and determine a position of the surgical instrument relative to the registration model. In some embodiments, the detecting and registering steps may be executed automatically by the processors without additional user input. In certain embodiments, the 3-D scanning device may communicate with the workstation during the non-contact patient registration method via a wireless or wired communication technique.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Figure 2:
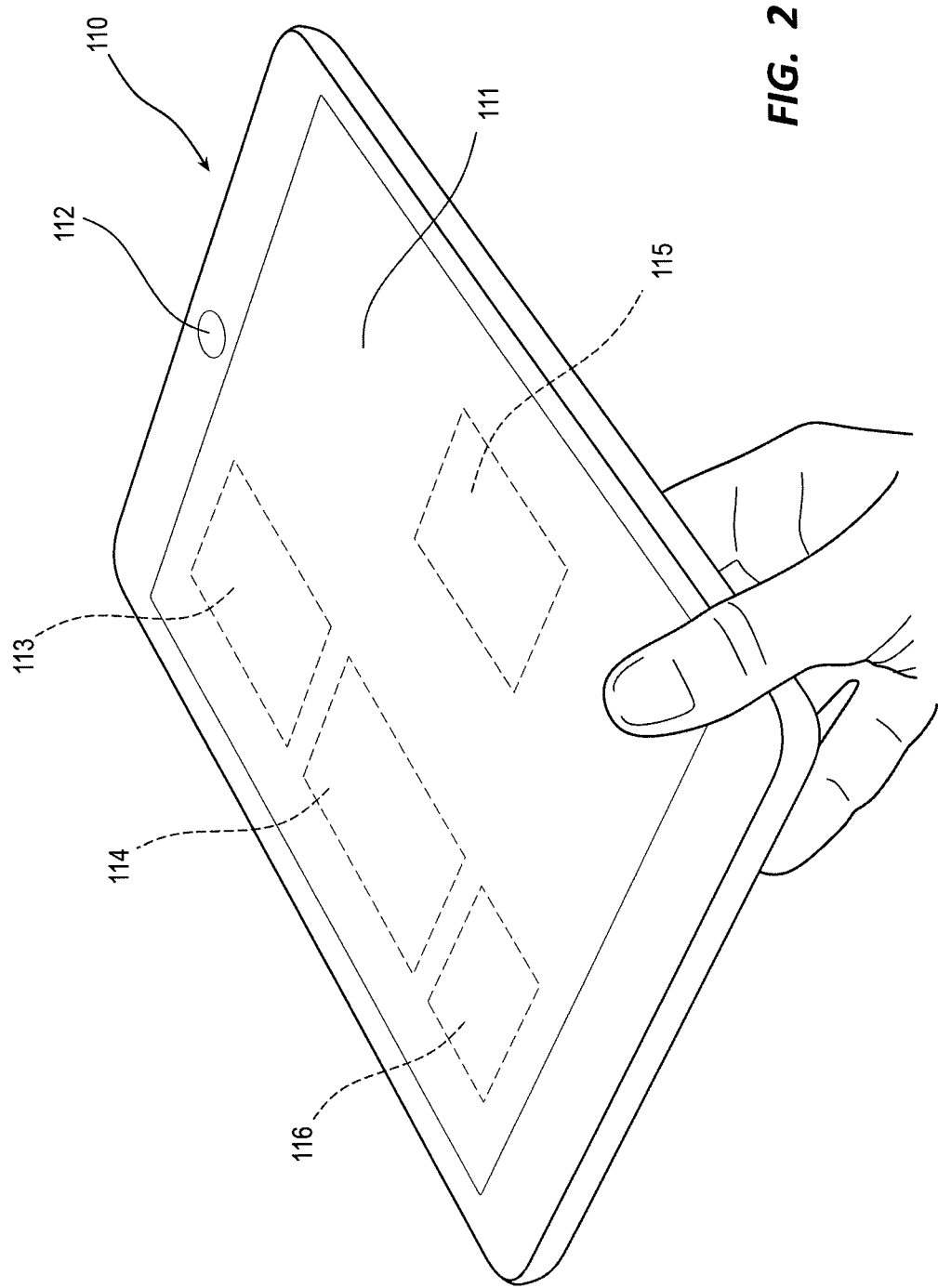
FIG. 2 is a perspective view of an embodiment of a 3-D scanning device of the non-contact patient registration system of FIG. 1.
Figure 3:
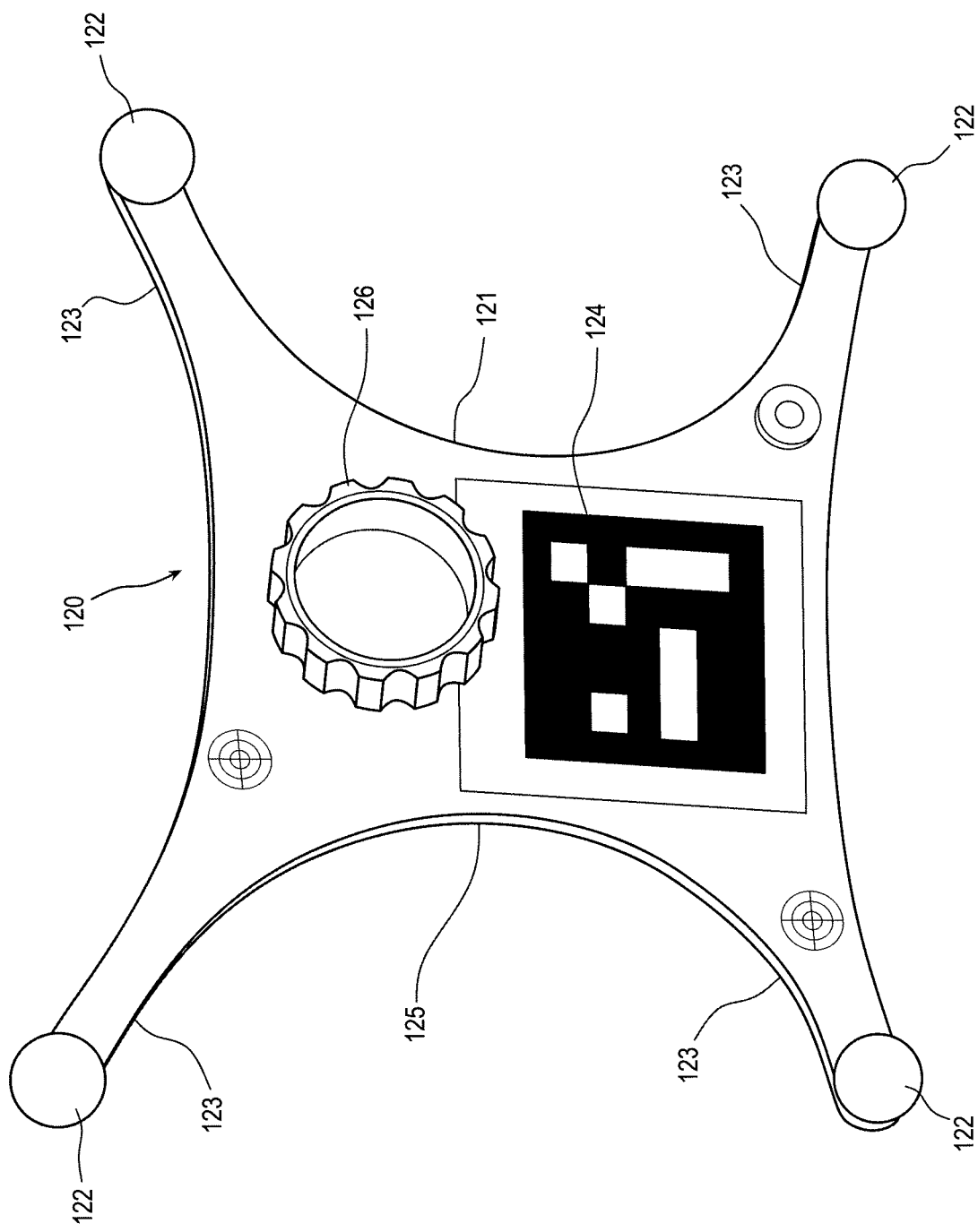
FIG. 3 is a perspective view of an embodiment of an optical reference frame of the non-contact patient registration system of FIG. 1.
Figure 4:
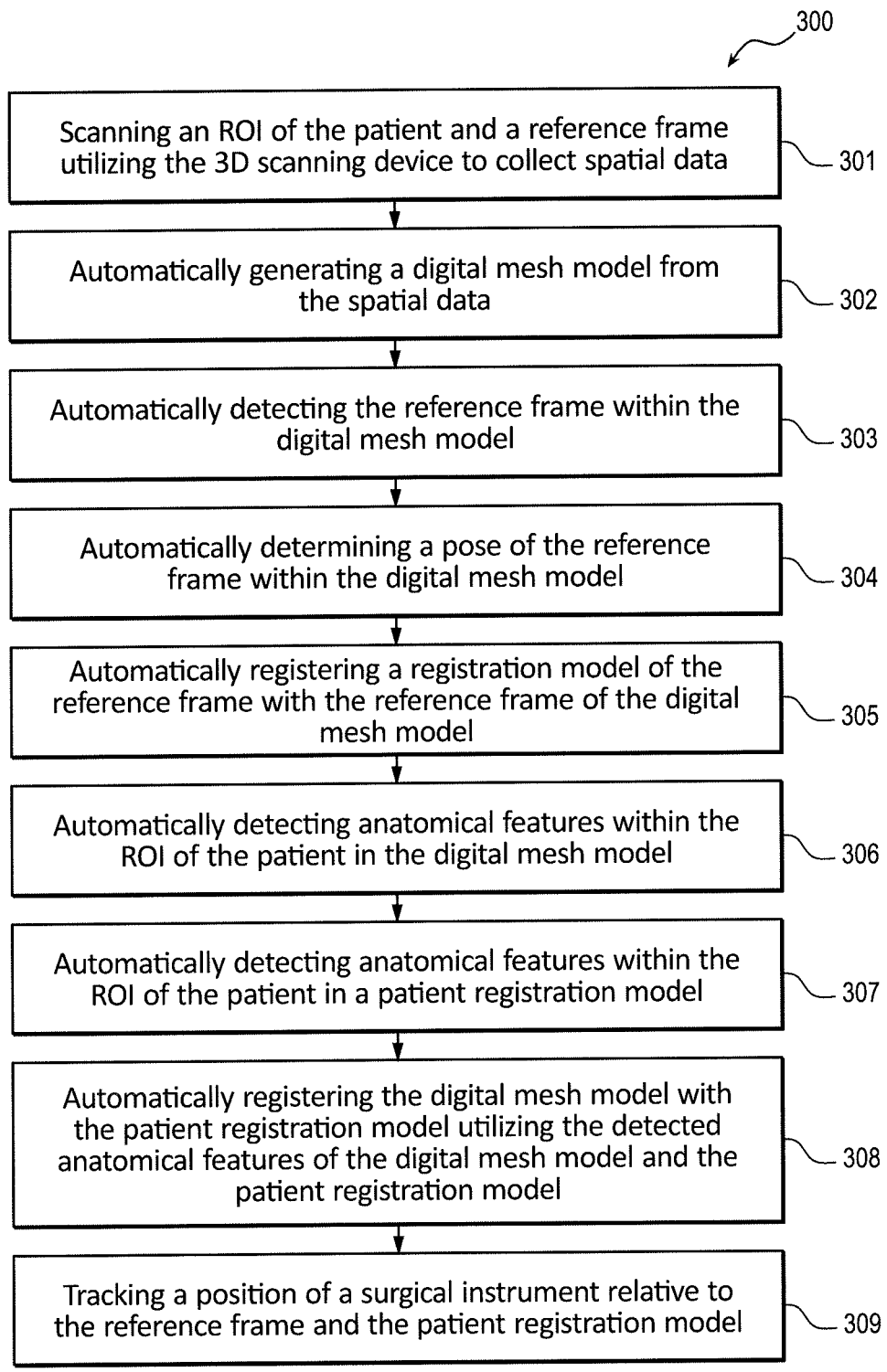
FIG. 4 is a flow chart of a method of non-contact patient registration.
Figure 5:
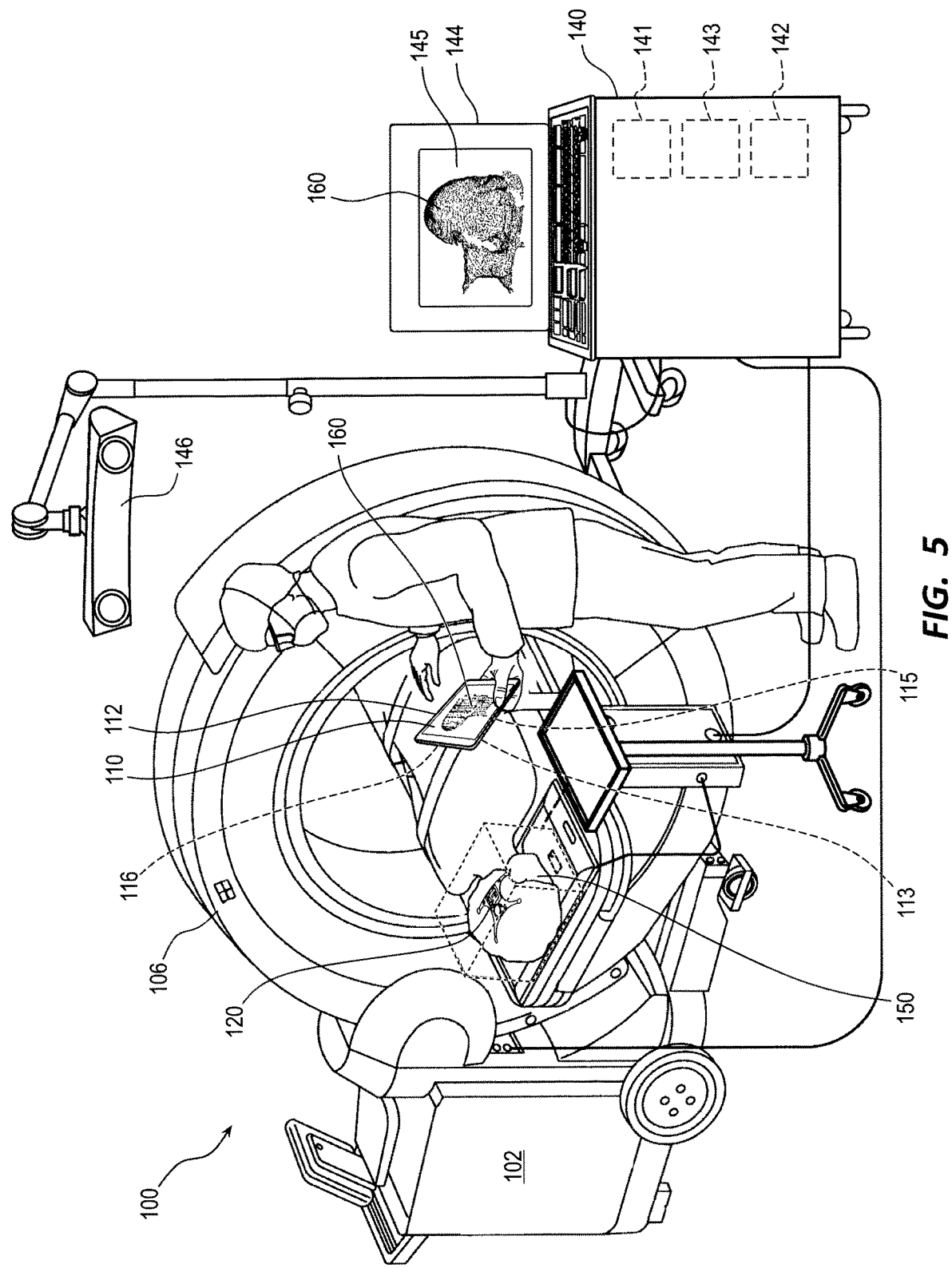
FIG. 5 is a schematic view of the surgical registration system of FIG. 1 during a step of the method of non-contact patient registration of FIG. 3 where the optical reference frame of FIG. 3 and a region of interest of a patient are spatially scanned with the 3-D scanning device of FIG. 2 to obtain spatial data points.
Figure 6:
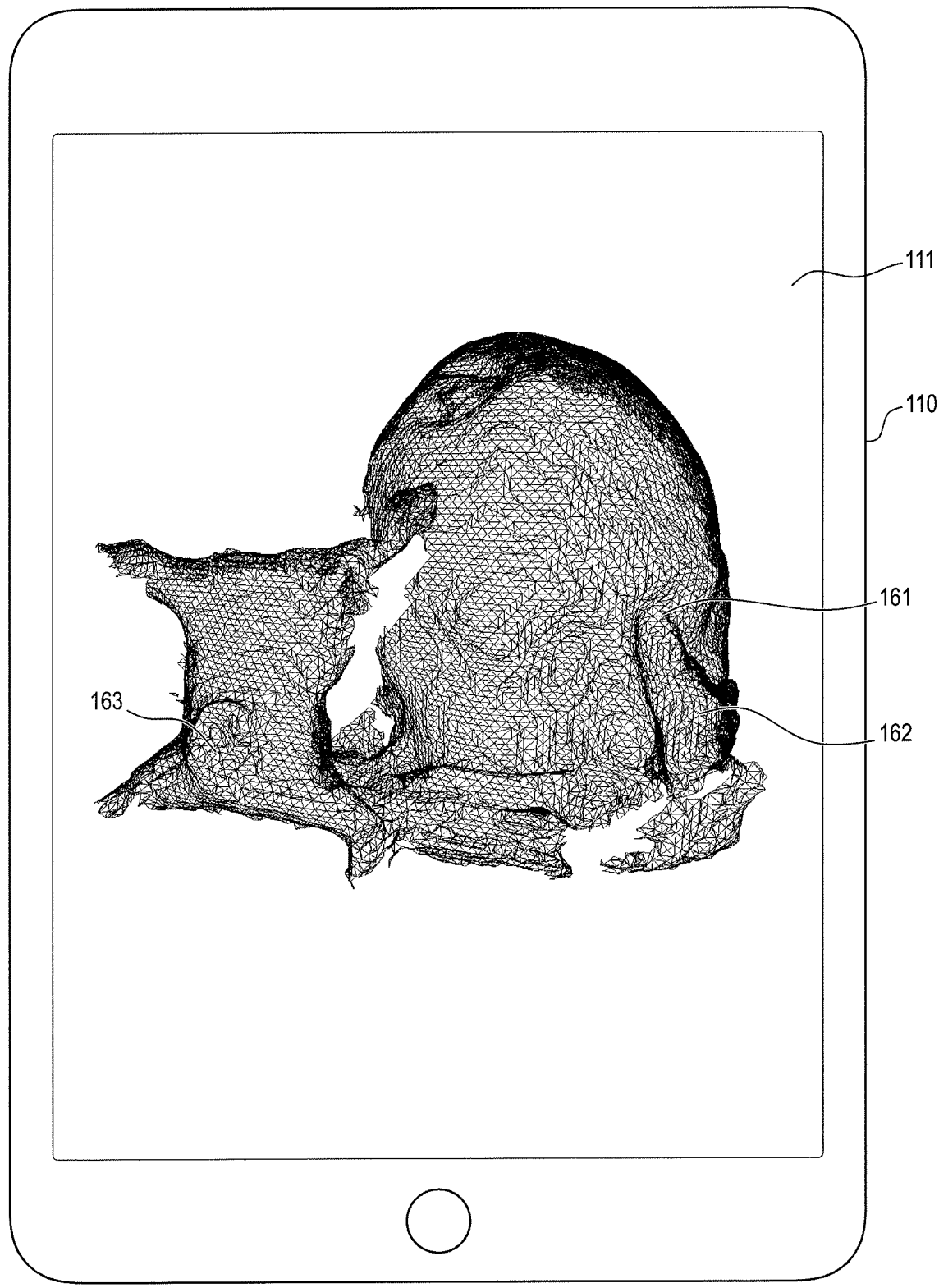
FIG. 6 is an output image of a step of the method of non-contact patient registration of FIG. 4 where a digital mesh model is generated from the spatial data points.
Figure 7:
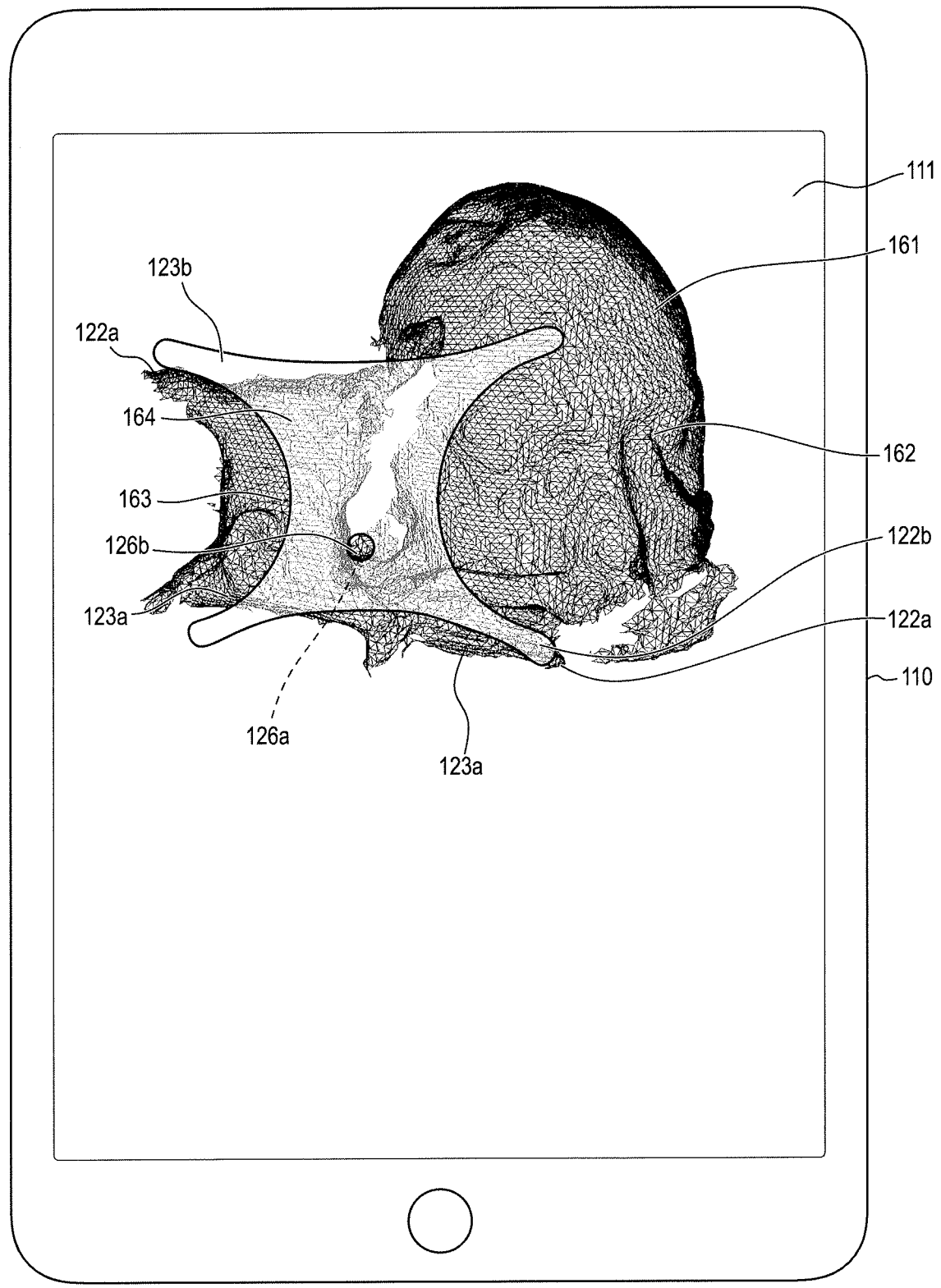
FIG. 7 is an output image of a step of the method of non-contact patient registration of FIG. 4 where a position of a reference frame mesh model is determined, and a reference frame registration model is registered with a reference frame mesh model.
Figure 8:
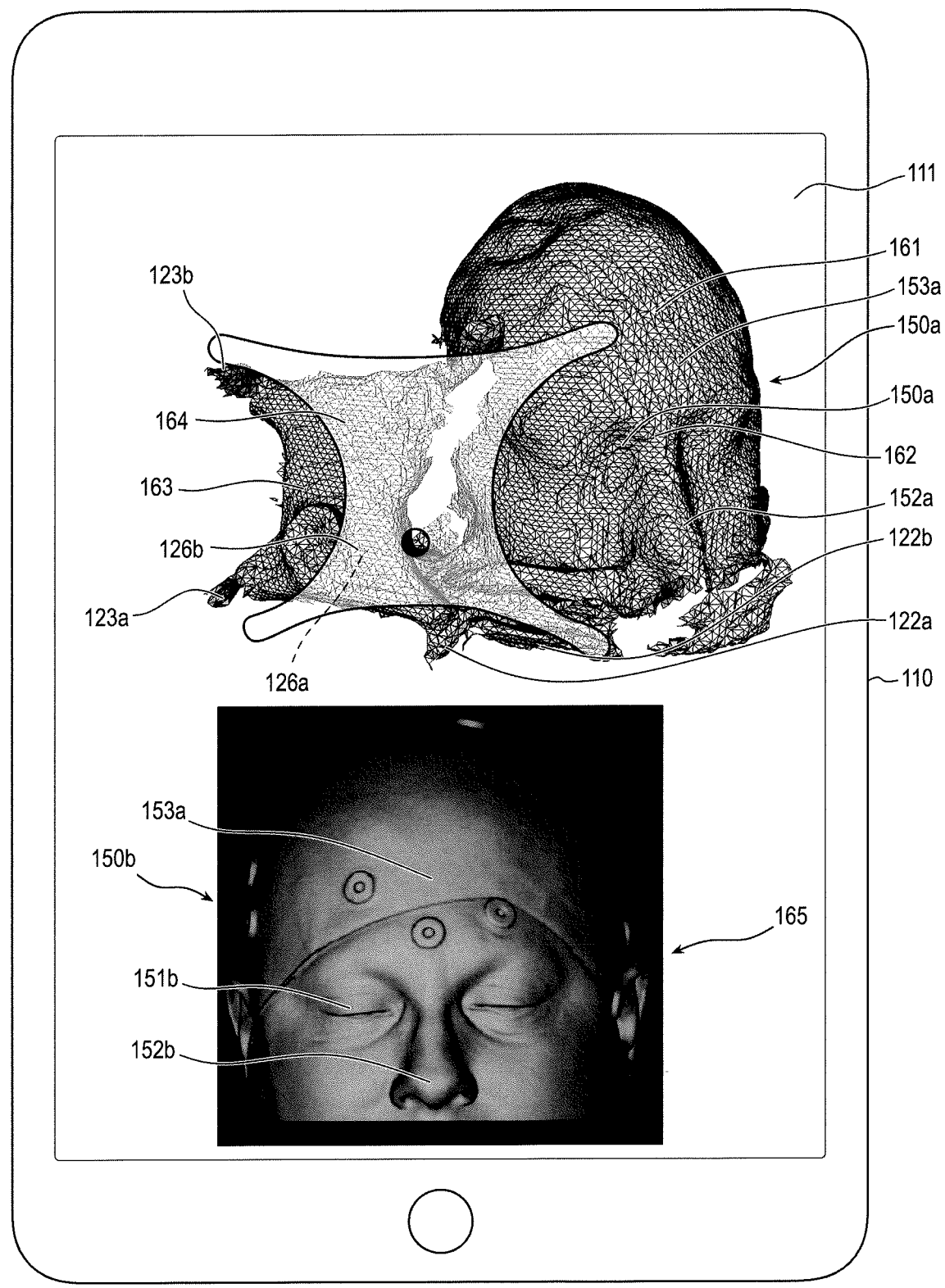
FIG. 8 is an output image of a step of the method of non-contact patient registration of FIG. 4 where anatomical features of the digital mesh model and a patient registration model are identified.
Figure 9:
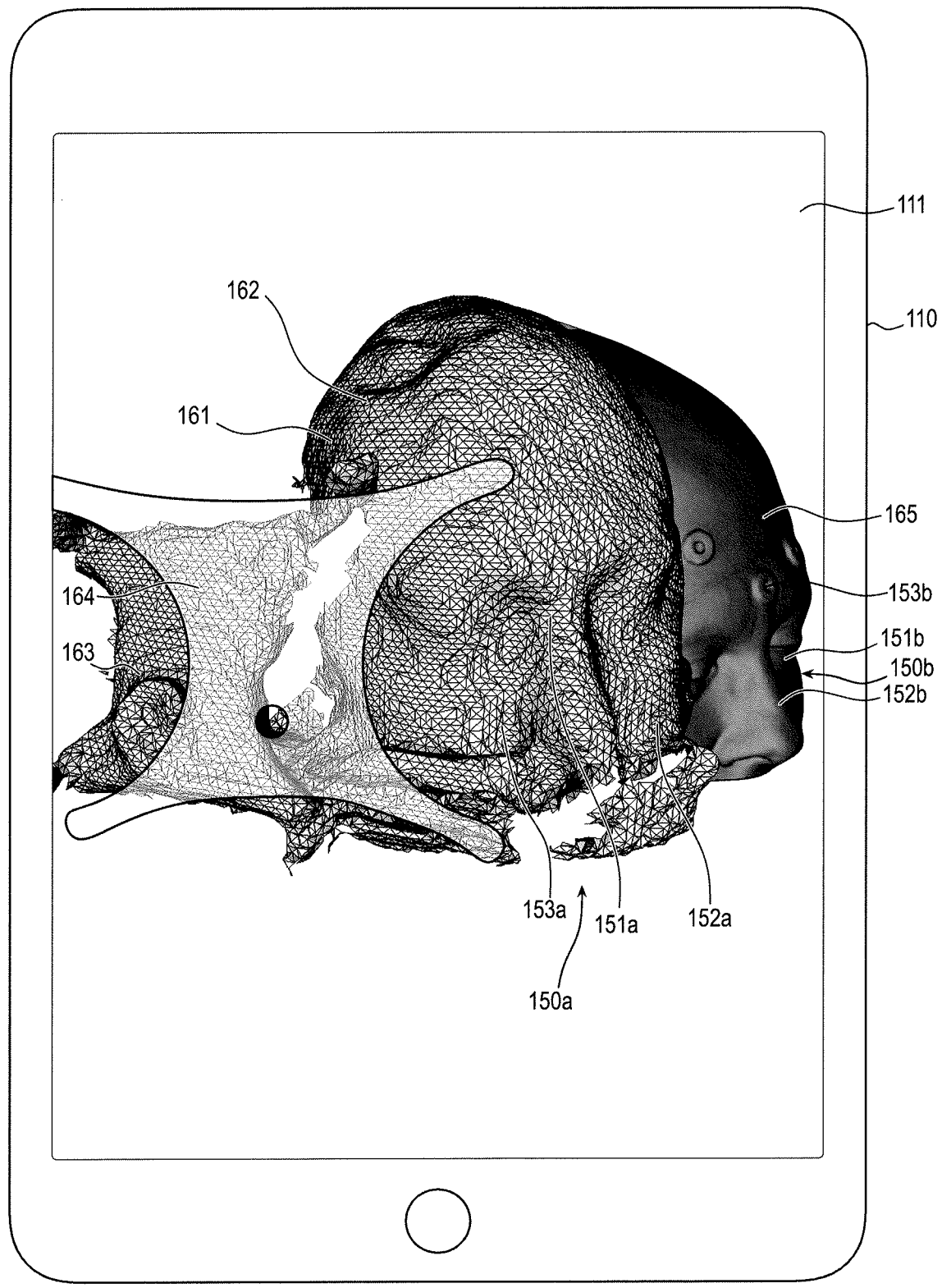
FIG. 9 is an output image of a step of the method of non-contact patient registration of FIG. 4 where the digital mesh model is partially registered with the patient registration model.
Figure 10:
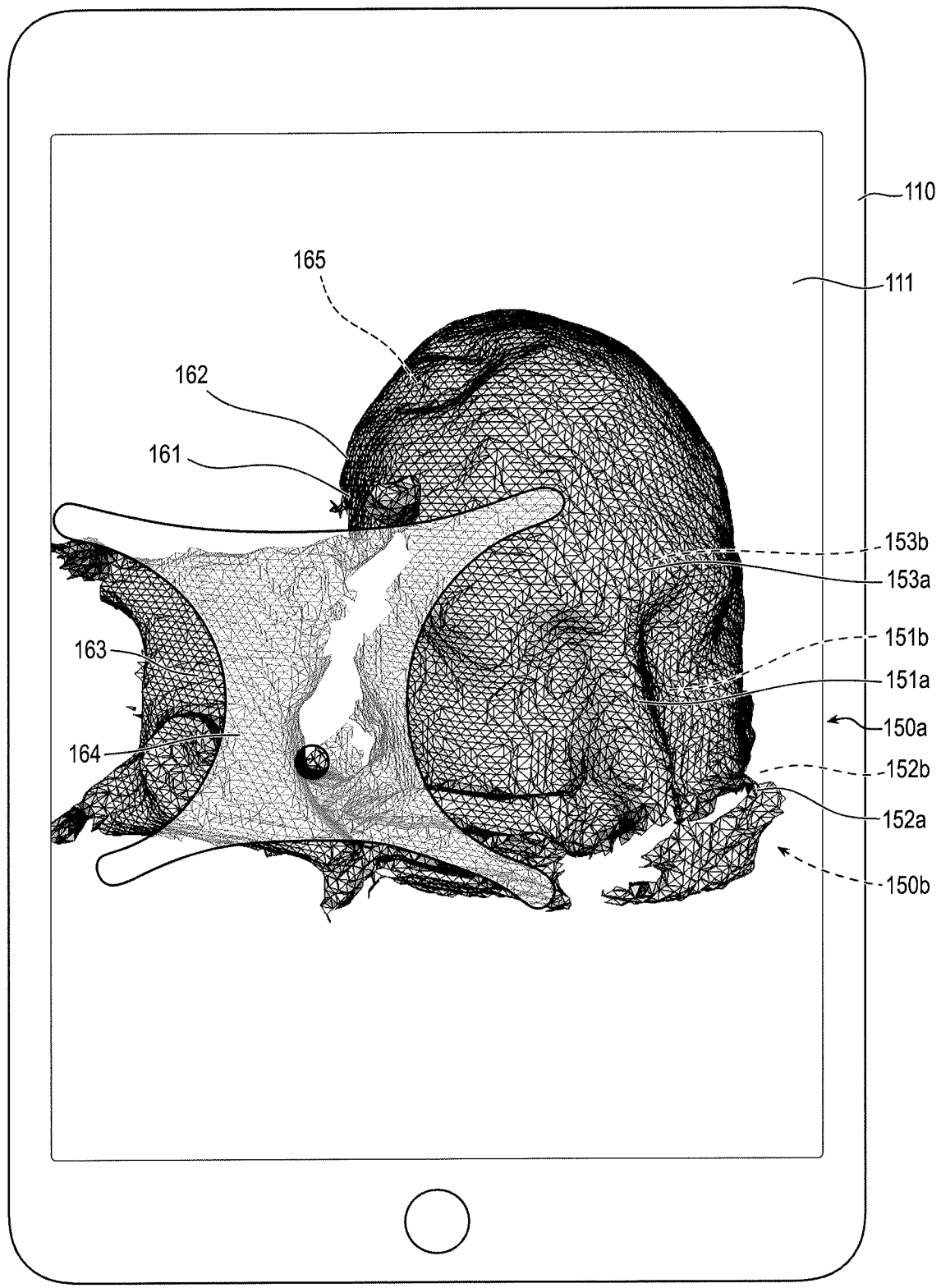
FIG. 10 is an output image of a step of the method of non-contact patient registration of FIG. 4 where the digital mesh model is fully registered with the patient registration model.
Figure 11:
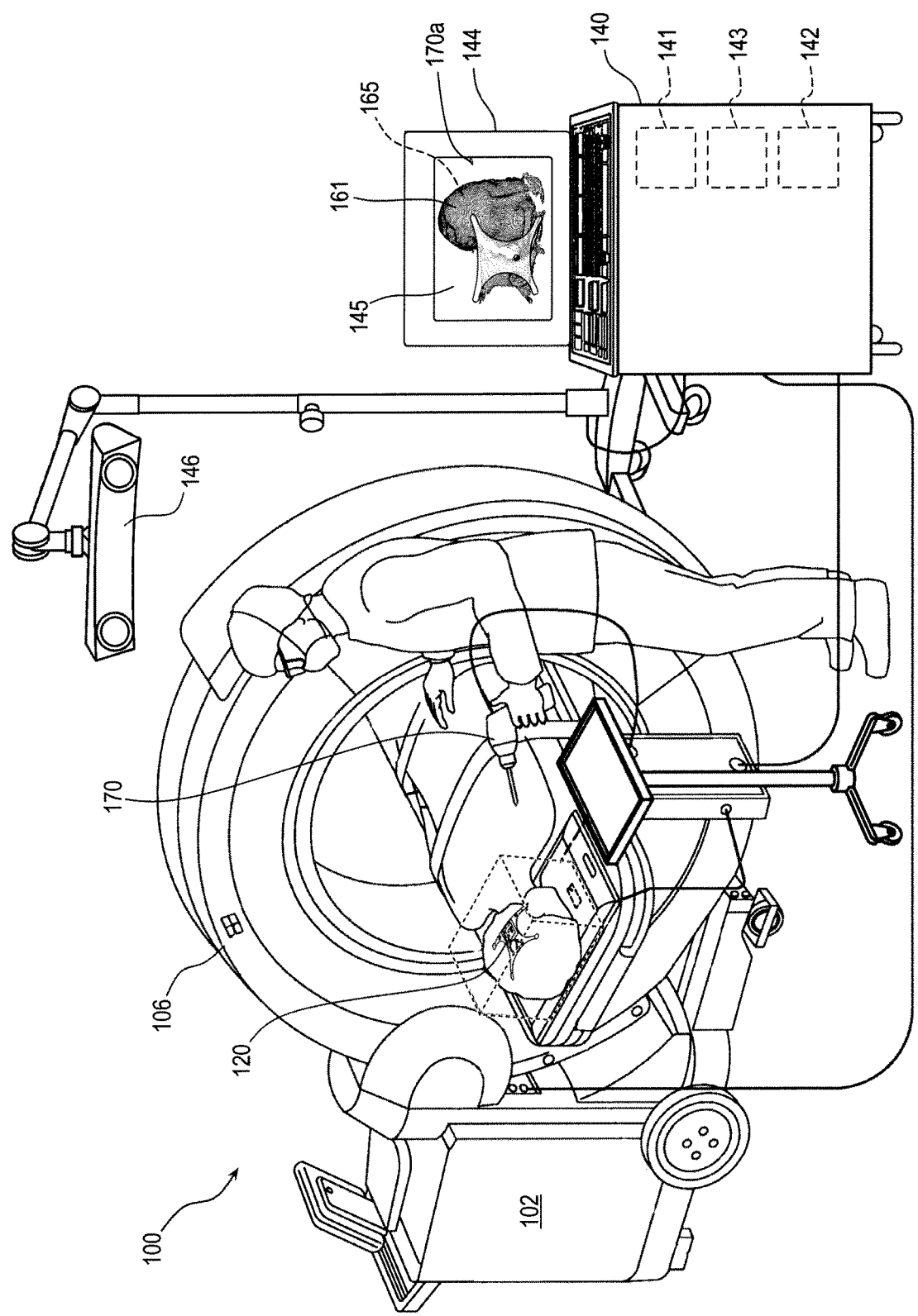
FIG. 11 is a schematic view of the non-contact patient registration system of FIG. 1 where a position of a surgical instrument is tracked relative to the reference frame and patient registration model.
Figure 12:
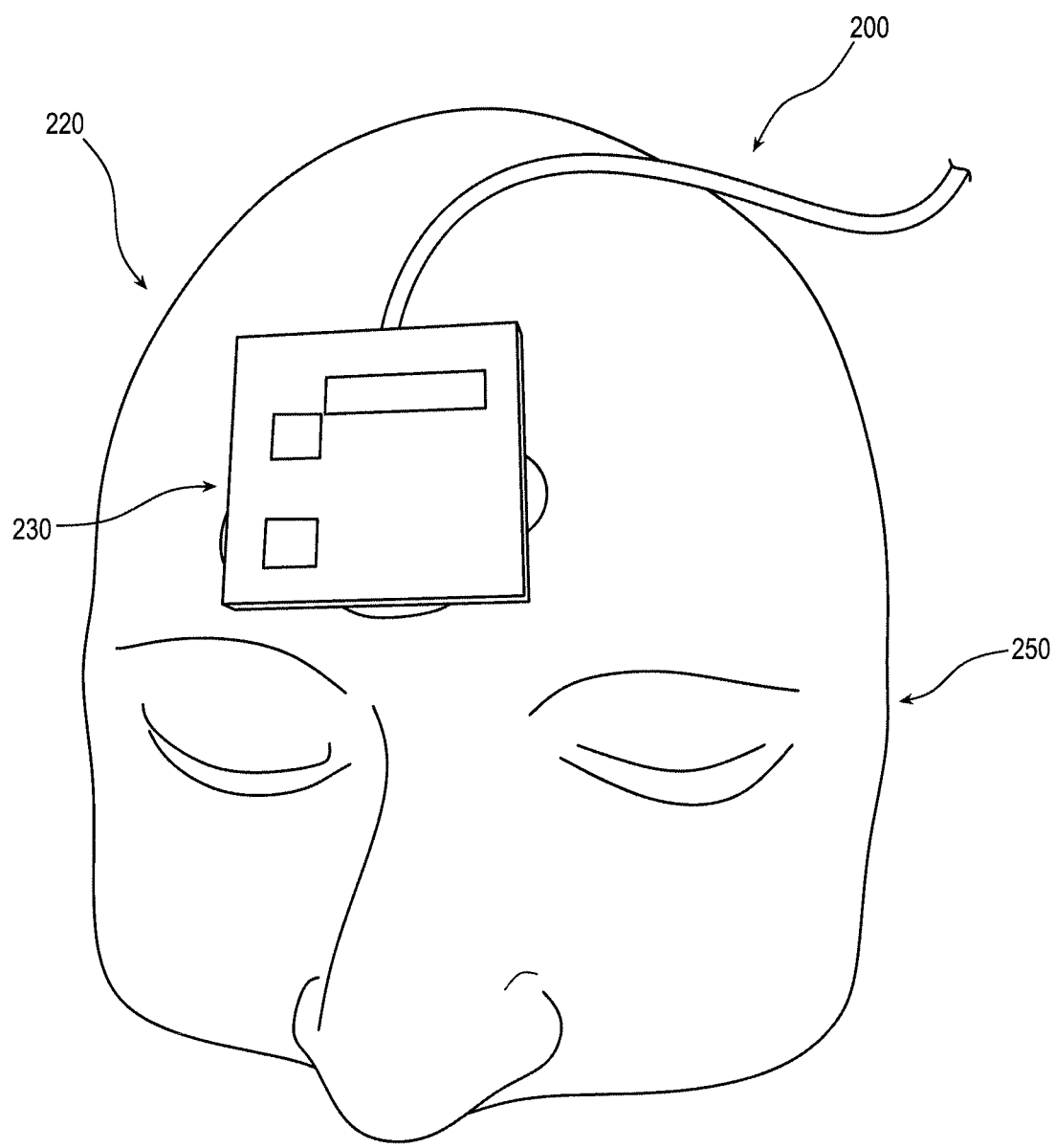
FIG. 12 is a schematic view of another embodiment of a non-contact patient registration system.
Figure 13:
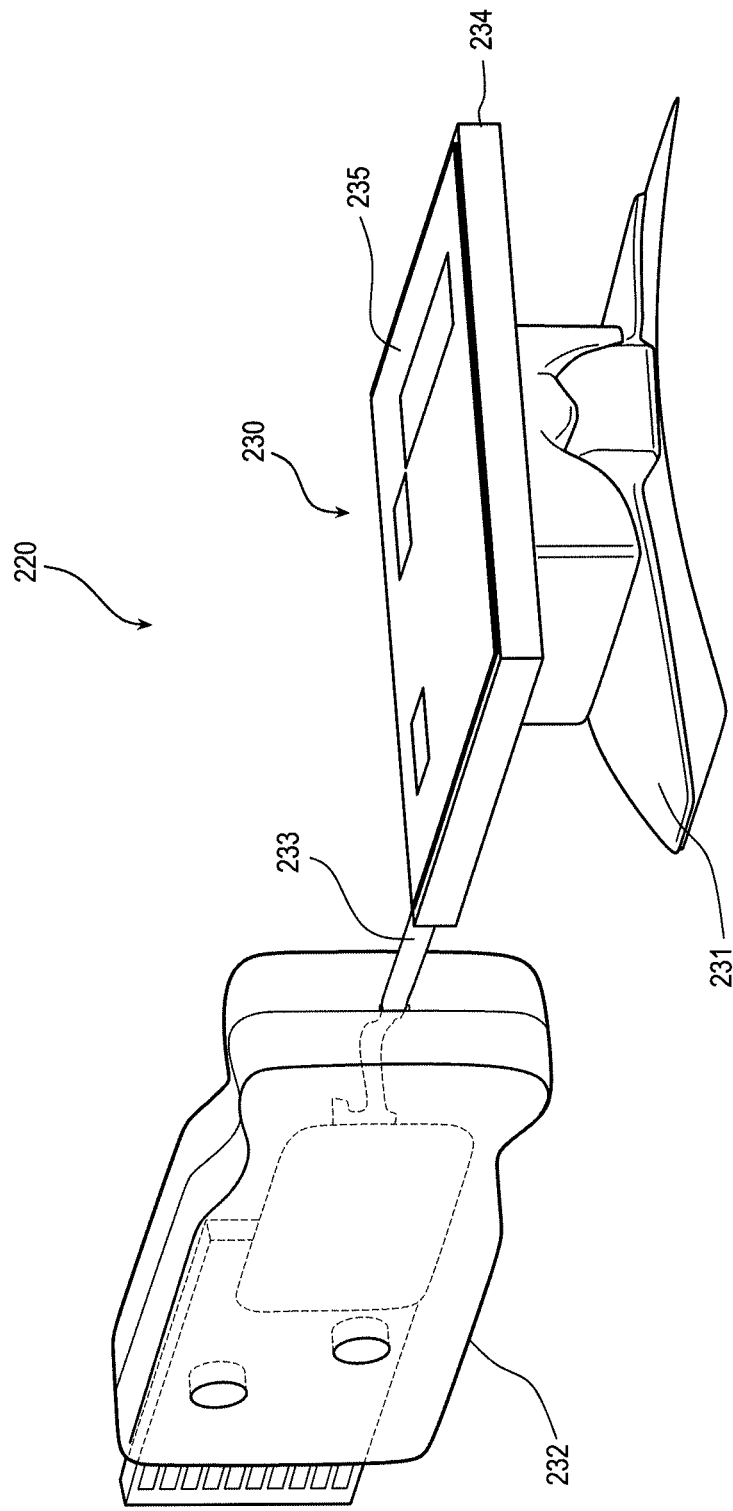
FIG. 13 is a perspective view of an electromagnetic reference frame with an ArUco optical tracker attachment of the surgical registration system of FIG. 12.

FIG. 1 schematically illustrates an embodiment of a non-contact patient registration system. FIG. 2. Illustrates an embodiment of a 3-D scanning device of the non-contact patient registration system. FIG. 3 illustrates an embodiment of an optical reference frame of the non-contact patient registration system. FIG. 4 illustrates a flow chart of a method of non-contact patient registration. FIG. 5 schematically illustrates the surgical registration system during a step of the method of non-contact patient registration where a reference frame and an ROI of a patient are spatially scanned to obtain spatial data points. FIG. 6 depicts an output image of a step of the method of non-contact patient registration where a digital mesh model is generated from the spatial data points. FIG. 7 depicts an output image of a step of the method of non-contact patient registration where a position of a reference frame mesh model is determined, and a reference frame registration model is registered with a reference frame mesh model. FIG. 8 depicts an output image of a step of the method of non-contact patient registration where anatomical features of the digital mesh model and a patient registration model are identified. FIG. 9 depicts an output image of a step of the method of non-contact patient registration where the digital mesh model is partially registered with the patient registration model. FIG. 10 depicts an output image of a step of the method of non-contact patient registration where the digital mesh model is fully registered with the patient registration model. FIG. 11 schematically illustrates the surgical registration system where a position of a surgical instrument is tracked relative to the reference frame and patient registration model. FIG. 12 schematically illustrates another embodiment of a non-contact patient registration system including an EM reference frame. FIG. 13 illustrates the EM reference frame. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 illustrates an embodiment of a non-contact patient registration system 100. As illustrated, the non-contact patient registration system 100 can include a 3-D scanning device 110, a reference frame 120, and a workstation 140. The non-contact patient registration system 100 is shown in an exemplary surgical environment that may include an image processor 102, an optical navigation device 146, an intraoperative 3-D imaging device, such as a computed tomography scanner.

FIG. 2 illustrates an embodiment of the 3-D scanning device 110. The 3-D scanning device 110 can be a handheld computing device, such as a camera, a smart phone having an integrated camera, a digital computer pad (e.g., tablet) having an integrated camera, a laptop computer coupled to a camera, standalone 3-D scanner, etc. In certain embodiments, the 3-D scanning device 110 can be coupled to a handle to facilitate manipulation of the 3-D scanning device 110 by a user. Manipulation of the 3-D scanning device 110 can include lateral, vertical, circular, arcuate, and other movements to capture spatial data of the ROI. In some embodiments, the movements of the optical scanning device 110 are not tracked by the optical scanning device 110 or any other tracking system. In other embodiments, the optical scanning device 110 may be mounted to a stationary stand.

As depicted in FIG. 2, the 3-D scanning device 110 includes a screen 111, a camera 113, a lens 112 coupled to the camera 113, a processor 114, a storage device 115, and a wireless communication device 116. The 3-D scanning device 110 is sized and configured to be held by one hand or by two hands for manual manipulation during operation. The 3-D scanning device 110 is free of or does not include any type of location tracker or reference marker. For example, the 3-D scanning device 110 is free of or does not include a tracker or reference marker such that a position or location of the 3-D scanning device 110 can be tracked using optical, electromagnetic, sonic, etc. position or tracking techniques. The camera 113 can be of any suitable type configured to digitally capture spatial data received through the lens 112. For example, the camera 113 may include a digital semiconductor image sensor, such as a charge coupled device (CCD) sensor or a complementary metal oxide semiconductor (CMOS) sensor configured to capture light through the lens 112 and convert the light into spatial data, such as an spatial data cloud. Other sensors, such as laser imaging, detection, and ranging (lidar), structured light, optical/infrared wavelength, etc., are within the scope of this disclosure. The lens 112 may be of any suitable type to transmit light to the camera 113. For example, the lens 112 may be a macro lens, a telephoto lens, a wide-angle lens, a fisheye lens, etc. In some embodiments the lens 112 is electronically controlled (e.g., focusing, zooming, etc.) by the 3-D scanning device 110. In other embodiments, the lens 112 is manually controlled by the user.

The processor 114 can be any suitable type configured to receive and execute instructions from the storage device 115. For example, the processor 114 can be similar to a processor used by a commercial smart phone or tablet device. For example, the processor may be Arm-based or Intel-based. The storage device 115 can be any suitable type configured to store the instructions to be executed by the processor 114 and to store the spatial data received from the camera 113. For example, the storage device 115 can be flash, ROM, PROM, EPROM, EEPROM, DRAM, SRAM, and any combination thereof. Other types of storage are contemplated.

The screen 111 may be configured to visually display information generated by the processor 114. The screen 111 may include a liquid crystal display (LCD), an organic light-emitting diode (OLED), or any other suitable display material. The screen 111 may be non-interactive or interactive (e.g., touch screen) and sized to be easily readable. A diagonal dimension of the screen 111 can range from about 4 inches to about 10 inches.

The wireless communication device 116 can include any suitable component to allow the 3-D scanning device 110 to wirelessly communicate information with the workstation 140 and to allow the workstation 140 to wirelessly communicate information with the 3-D scanning device 110. The information may include spatial data, digital mesh models, registration models, etc. as will be further described below. The communication can be via WiFi or Bluetooth. Other wireless communication techniques are within the scope of this disclosure. The wireless communication device 116 may include a WiFi module or a Bluetooth circuit. In other embodiments, the 3-D scanning device 110 can be in direct communication with the workstation 140 via a cable coupled to the 3-D scanning device 110 and the workstation 140.

As illustrated in FIG. 1, the workstation 140 can be remotely disposed from and be in wireless communication with the 3-D scanning device 110. The workstation 140 may include a processor 141, a storage device 142, and a wireless communication device 143. The processor 141 can be any suitable type configured to receive and execute instructions from the storage device 142. For example, the processor 141 can be Intel-based. Other processor types are contemplated. The storage device 142 can be any suitable type configured to store the instructions to be executed by the processor 141 and to store the spatial data and digital mesh models received from the 3-D scanning device 110, a patient registration image, a reference frame registration image, and so forth. For example, the storage device 142 can be flash, ROM, PROM, EPROM, EEPROM, DRAM, SRAM, and any combination thereof. Other types of storage are contemplated. The wireless communication device 143 can include any suitable component to allow the 3-D scanning device 110 to wirelessly communicate information with the workstation 140 and to allow the workstation 140 to wirelessly communicate information with the 3-D scanning device 110. The information may include the spatial data and digital mesh models received from the optical scanning device 110, a pre-operative image, a reference frame registration image, and so forth. The communication can be via WiFi or Bluetooth wireless techniques. Other wireless communication techniques are within the scope of this disclosures. The wireless communication device 143 may include a WiFi module or a Bluetooth circuit. In other embodiments, the optical scanning device 110 can be in direct communication with the workstation 140 via a cable coupled to the optical scanning device 110 and the workstation 140. In some embodiments, the workstation 140 may include a monitor to display information from the processor 141 and/or storage device 142. In some embodiments, the non-contact patient registration system 100 may not include a workstation 140. In such an embodiment, the 3-D scanning device 110 can be configured to perform all of the operations required for non-contact patient registration as disclosed herein.

FIG. 3 illustrates an embodiment of the optical reference frame 120. As illustrated, the optical reference frame 120 can include a structure 121. In the illustrated embodiments, the structure 121 includes a geometrical shape having a body portion 125, four arm members 123 extending radially outward from the body portion 125, and a knob 126 disposed on the body portion 125. In other embodiments, the structure 121 may include two, three, five, or more arm members 123. A reflector 122 may be disposed at an end of each of the arm members 123. The reflectors 122 may be configured to be detected by an optical tracking camera during a navigated surgical procedure. In some embodiments, at least one arm member 123 of the structure 121 can be coupled to a head holder to stabilize the structure 121 relative to the patient's head being held in the head holder. In other embodiments, the structure 121 can be coupled to the head holder at three of the arm members 123 with the fourth arm member 123 being disposed adjacent the patient's head. In still other embodiments, the knob 126 may be coupled to the headframe or the patient table using a fastener, such as a screw. Other geometrical shapes are contemplated within the scope of this disclosure. For example, the structure 121 may have a circular shape, an elliptical shape, a triangular shape, a quadrilateral shape, a pentagonal shape, and so forth. In the depicted embodiment, the structure 121 includes an identifying label 124 to indicate an orientation of the structure 121. In another embodiment, the structure 121 may include a two-dimensional quick response (QR) label (e.g., ArUco marker) to provide coordinates of the QR label within a visual field as captured by a scanning device. In some embodiments, identifying label 124 may be color-coded.

FIG. 4 illustrates a flow chart depicting steps of a method 300 to generate a digital mesh model of the ROI of a patient and a reference frame and to register a digital mesh model with patient and reference frame registration models. As depicted the method can include one or more of the following: scanning 301 the ROI of the patient and the reference frame utilizing the optical scanning device to collect spatial data; automatically generating 302 a digital mesh model from a three-dimensional cloud point image of the spatial data; automatically detecting 303 the reference frame within the digital mesh model; automatically determining 304 a pose (e.g., position and orientation) of the optical reference frame within the digital mesh model; automatically registering 305 a registration model of the reference frame with the optical reference frame of the digital mesh model; automatically detecting and weighting 306 anatomical features within the ROI of the patient in the digital mesh model; automatically detecting and weighting 307 anatomical features within the ROI of the patient in a patient registration model; automatically registering 308 the digital mesh model with the patient registration model utilizing the detected anatomical features of the digital mesh model and the patient registration model; and tracking 309 a position of a surgical instrument relative to the reference frame and the patient registration model. In certain embodiments, the steps of the workflow can be executed by the 3-D scanning device 110 with various images displayed on the screen 111 of the 3-D scanning device 110. In other embodiments, certain steps of the workflow can be executed by the 3-D scanning device 110 with various associated images displayed on the screen 111 and other steps of the workflow can be executed by the workstation 140 with various associated images displayed on a screen 145 of a monitor 144 of the workstation 140, as shown in FIG. 1.

FIG. 5 illustrates an ROI 150 spatially scanned by the 3-D scanning device 110. In the illustrated embodiment, the user can hold the 3-D scanning device 110 in a single hand or in two hands with the lens 112 directed toward the ROI 150 and the optical reference frame 120 and move the 3-D scanning device 110 in any direction that may facilitate capture of spatial data points of the ROI 150 and the optical reference frame 120 by the camera 113. For example, the 3-D scanning device 110 can be moved laterally, vertically, arcuately, and/or circularly. In another embodiment, the 3-D scanning device 110 may be coupled to a stationary stand to scan the ROI 150 and the optical reference frame 120 from a single vantage point or over a predetermined range of positions. The spatial data points can be stored in the storage device 115. In another embodiment, the spatial data points may be transmitted to the workstation 140 via the wireless communication devices 116, 143 and stored in the storage device 142. The number of spatial data points captured by the 3-D scanning device 110 can range from about 10,000 to about 100,000 or more. The spatial data points can be displayed on the screen 111 as a three-dimensional (3D) or two-dimensional (2D) 160 image of the ROI 150 and the optical reference frame 120. The spatial data points are without any information regarding the location of the 3-D scanning device 110 relative to the ROI and the optical reference frame 120.

As illustrated in FIG. 6, following capture and storage of the spatial data points, the processor 114 or 141 may automatically generate a 30 or 2D digital mesh model 161 from the spatial data points. The digital mesh model 161 may include an ROI mesh model 162 and a reference frame mesh model 163. The digital mesh model 161 may be displayed on the screen 111 of the 3-D scanning device 110. In other embodiments, the processor 141 may generate the digital mesh model 161 and display on the screen or monitor 145 coupled to the workstation 140.

As illustrated in FIG. 7, following generation of the digital mesh model 161, the processor 114 or 141 can automatically determine a pose of the reference frame mesh model 163 within the digital mesh model 161 and identify features of the reference frame mesh model 163. The identified features can include reflectors 122a, arm members 123a, and/or knob 126a. Other features are contemplated. The processor 141 can retrieve a reference frame registration model 164 from the storage device 142 and register the reference frame registration model 164 with the reference frame mesh model 163. The registration can be accomplished by alignment of the identified features (e.g., reflectors 122a, arm members 123a, and knob 126a) of the reference frame mesh model 163 with corresponding features (e.g., reflectors 122b, arm members 123b, and knob 126b) of the reference frame registration model 164. The registered models 163, 164 can be displayed on the screen 145 of the monitor 144 and/or the registered models 163, 164 may be displayed on the screen 111. In some embodiments, the reference frame registration model 164 may be generated utilizing any suitable technique, such as computer-aided design (CAD).

As illustrated in FIG. 8, the processor 114 or 141 can automatically identify anatomical features of an ROI 150 *a* of the ROI mesh model 162 using a facial recognition algorithm. The anatomical features can include an eye 151 *a*, a nose 152 *a*, and a forehead 153 *a*. Other anatomical features, such as a corner of a mouth, other portions of a mouth, an ear, a cheek, etc., are contemplated dependent on the location of the ROI 150. The processor 141 can retrieve a patient registration model 165 from the storage device 115 or 142 and identify anatomical features of an ROI 150 *b* of the patient registration model 165 using the facial recognition algorithm. The anatomical features can include, for example, an eye 151 *b*, a nose 152 *b*, and a forehead 153 *b*. Other anatomical features are contemplated dependent on the location of the ROI 150 *b*, such as an ear, a mouth, an eyebrow, a jaw, etc. In certain embodiments, the patient registration model 165 can be a 3-D or 2-D model of the ROI 150 *b* generated from any suitable medical imaging technique, such as CT, MRI, computer tomography angiography (CTA), magnetic resonance angiography (MRA), functional magnetic resonance imaging (fMRI), positron emission tomography (PET), single photon emission computed tomography (SPECT) intraoperative CT, etc.

In some embodiments, the identified anatomical features of the ROI mesh model 162 and the patient registration model 165 can be weighted by the facial detection algorithm to increase the accuracy of registration of the models 162, 165. The weighting of the anatomical features can be based on a level of repeatability of a position of the anatomical features relative to the ROI. For example, the pose of certain anatomical features (e.g., cheek region, jaw region, back of head region ear region), change more from one patient pose to another, and thus the pose of those features depends more on the pose of the patient when scanned. The facial recognition algorithm may weigh these anatomical features lower or with less importance than other anatomical features that demonstrate less variability. Anatomic features that demonstrate more variability and are given less weight in some embodiments may be referred to as "low weighted anatomical features." Further, the pose of other anatomical features (e.g., ridges around the eyes, eyebrows, forehead region, mouth, and/or nose) changes less from one patient pose to another, and thus the pose of those features depends less on the pose of the patient when scanned. Anatomic features that demonstrate less variability and are given more weight in some embodiments may be referred to as "high weighted anatomical features." In certain embodiments, some or all of the low weighted anatomical features may be deleted from the facial detection algorithm, such that they are not utilized in the registration process.

As illustrated in FIGS. 9 and 10, the processor 114 or 141 can automatically register the ROI mesh model 162 with the patient registration model 165 by aligning the anatomical features 150 (e.g., the eye 151a, the nose 152a, the forehead 153a) detected and weighted by the facial detection algorithm within the ROI mesh model 162 with the anatomical features (e.g., the eye 151b, the nose 152b, the forehead 153b) detected and weighted by the facial detection algorithm within the patient registration model 165. In other words, the high weighted anatomical features of the ROI mesh model 162 and the corresponding high weighted anatomical features of the patient registration model 165 may be utilized to primarily align or register the ROI mesh model 162 with the patient registration model 165. In some embodiments, the low weighted anatomical features of the ROI mesh model 162 and the patient registration model 165 may be utilized as secondary alignment or registration features. FIG. 9 depicts partial registration of the ROI mesh model 162 with the patient registration model 165. FIG. 10 illustrates full registration of the ROI mesh model 162 with the patient registration model 165 where the anatomical features (e.g., the eye 151a, the nose 152a, the forehead 153a) of the ROI mesh model 162 are aligned with the anatomical features (e.g., the eye 151b, the nose 152b, the forehead 153b) of the patient registration model 165. The registration also results in registration of the reference frame mesh model 163 relative to the patient registration model 165 such that a location of the optical reference frame 120 is known relative to the patient registration model 165.

As illustrated in FIG. 11, following registration of the digital mesh model 161 with the patient registration model 165, a pose of a surgical instrument 170 may be visually tracked relative to the optical reference frame 120 using an optical navigation device 146. The surgical instrument 170 can be displayed as a surgical instrument model 170a on the screen 145 of the monitor 144 of the workstation 140.

FIGS. 12 and 13 depict an embodiment of a surgical registration system 200 that resembles the non-contact patient registration system 100 described above in certain respects. Accordingly, like features are designated with like reference numerals, with the leading digit incremented to "2." For example, the embodiment depicted in FIGS. 12 and 13 includes a reference frame 220 that may, in some respects, resemble the optical reference frame 120 of FIG. 1. Relevant disclosure set forth above regarding similarly identified features thus may not be repeated hereafter. Moreover, specific features of the optical reference frame 120 and related components shown in FIGS. 1-11 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the non-contact patient registration system 200 and related components depicted in FIGS. 12 and 13. Any suitable combination of the features, and variations of the same, described with respect to the non-contact patient registration system 100 and related components illustrated in FIGS. 1-11 can be employed with the non-contact patient registration system 200 and related components of FIGS. 12 and 13, and vice versa.

FIG. 12 depicts another embodiment of a non-contact patient registration system 200. As illustrated, the non-contact registration system 200 can include a reference frame 220. The reference frame 220 may be coupled to a patient and disposed within an ROI 250 of the patient. The reference frame 220 may include an EM reference frame 230. As illustrated in FIG. 13, the EM reference frame 230 includes an EM tracker member 231 and an attachment 234 coupled to the EM tracker member 231. The EM tracker member 231 may include an adhesive surface configured to adhere the EM tracker member 231 to the patient. An electronic connector 232 is coupled to the EM tracker member 231 via a cable 233. The electronic connector 232 may be configured to be coupled to a workstation 240 (not shown) to transmit electromagnetic data between the EM tracker member 231 and the workstation 240.

The attachment 234 can have a geometric shape such as a square shape or a rectangular shape. An upper surface of the base 234 may include a two-dimensional bar code 235 (e.g., ArUco marker). In certain embodiments, the two-dimensional bar code 235 is a QR code. The QR code can provide digital coordinates of a pose of the attachment 234 when optically scanned. In other words, the QR code can provide a pose of the reference frame 220. In some embodiments, the attachment 234 may be color-coded. In certain embodiments, the attachment 234 can include an adapter configured to selectively couple to the EM tracker member 231. The adapter can be coupled to the EM tracker member 231 utilizing any suitable technique.

For example, the adapter may be coupled via a snap fit, an adhesive, a rotation engagement, and a translational engagement. Other coupling techniques are considered. In some embodiments the attachment 234 may be removed from the EM tracker member 231 following registration of a digital mesh model with a patient registration model to avoid interference of the attachment 234 with surgical instruments utilized during a surgical procedure.

In use, a processor can determine the pose of the reference frame 220 relative to an ROI mesh model of a digital mesh model by utilizing the coordinates of the QR code—The QR code may be registered to the ROI mesh model by determining its pose within a coordinate system of the ROI mesh model. Based on the pose of the QR code, the pose of the reference frame within the ROI mesh model can be computed. The ROI mesh model may be registered to the registration model.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of non-contact patient registration, comprising spatially scanning a region of interest (ROI) of a patient and a reference frame using an 3-D scanning device to capture a collection of spatial data points; constructing a digital mesh model from the collection of spatial data points; determining a location and position of the reference frame within the digital mesh model; detecting anatomical features of the ROI of the digital mesh model and a patient registration model; registering the ROI of the digital mesh model with the patient registration model, wherein the detected anatomical features of the digital mesh model are aligned with the detected anatomical features of the patient registration model. Other steps are also contemplated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

It will be appreciated that various features are sometimes grouped together in a single embodiment, figure, or description thereof for the purpose of streamlining the disclosure. Many of these features may be used alone and/or in combination with one another.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

References to approximations are made throughout this specification, such as by use of the term "about." For each such reference, it is to be understood that, in some embodiments, the value, feature, or characteristic may be specified without approximation. For example, where the qualifier "about" is used, this term includes within its scope the qualified word in the absence of its qualifiers.

The terms "a" and "an" can be described as one, but not limited to one. For example, although the disclosure may recite a generator having "an electrode," the disclosure also contemplates that the generator can have two or more electrodes.

Unless otherwise stated, all ranges include both endpoints and all numbers between the endpoints.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A method of touchless registration for a surgical procedure, comprising:
    scanning a region of interest (ROI) of a patient and a reference frame using a 3-D scanning device to capture a collection of spatial data points;
    constructing an ROI digital mesh model from the collection of spatial data points;
    detecting the reference frame in the collection of spatial data points;
    constructing a reference frame digital mesh from the spatial data points;
    registering a reference frame registration model with the reference frame mesh model;
    detecting an anatomical feature of the ROI digital mesh model and a corresponding anatomical feature of a patient registration model utilizing a facial detection algorithm;
    weighting the anatomical feature of the ROI digital mesh model and the corresponding anatomical feature of the patient registration model; and
    registering the ROI digital mesh model with the patient registration model utilizing the weighted anatomical features of the ROI digital mesh model and the patient registration model to generate a navigation space;
    wherein the weighting of the anatomical feature is based on a level of repeatability of positions of the anatomical features relative to the ROI.

2. The method of claim 1, wherein the anatomical feature comprises any one of a region of a nose, a region of an eye, a region of an ear, a region of a mouth, region of a cheek, a region of an eyebrow, a region of a jaw, and any combination thereof.

3. The method of claim 1, further comprising creating the patient registration model from any one of computed tomography (CT), magnetic resonance image (MRI), computer tomography angiography (CTA), magnetic resonance angiography (MRA), intraoperative CT images.

4. The method of claim 1, further comprising:
    detecting a location and position of the reference frame digital mesh model within a digital mesh model.

5. The method of claim 1, further comprising displaying the registered reference frame registration model with the ROI digital mesh model.

6. The method of claim 4, wherein the digital mesh model comprises: the ROI digital mesh model; and
    the reference frame digital mesh model.

7. The method of claim 1, wherein the reference frame comprises a structure disposed adjacent the ROI.

8. The method of claim 1, wherein the reference frame comprises an electromagnetic (EM) reference frame or an optical reference frame coupled to the patient within the ROI.

9. A method of touchless registration for a surgical procedure, comprising:
    scanning a region of interest (ROI) of a patient and a reference frame using a 3-D scanning device to capture a collection of spatial data points;
    constructing an ROI digital mesh model from the collection of spatial data points;
    detecting the reference frame in the collection of spatial data points;
    detecting an anatomical feature of the ROI digital mesh model and a corresponding anatomical feature of a patient registration model utilizing a facial detection algorithm;
    weighting the anatomical feature of the ROI digital mesh model and the corresponding anatomical feature of the patient registration model; and
    registering the ROI digital mesh model with the patient registration model utilizing the weighted anatomical features of the ROI digital mesh model and the patient registration model to generate a navigation space;
    wherein the weighting of the anatomical feature is based on a level of repeatability of positions of the anatomical features relative to the ROI.

10. The method of claim 9, wherein the weighting is high when the position of the anatomical feature is repeatable relative to the ROI.

11. The method of claim 10, wherein in the high weighted anatomical feature comprises any one of the bony contours around an eye, an eyebrow, a nose, a forehead region and any combination thereof.

12. The method of claim 9, wherein the weighting is low when the position of the anatomical feature is variable relative to the ROI.

13. The method of claim 12, wherein the low weighted anatomical feature is removed from the facial detection algorithm.

14. The method of claim 12, wherein the low weighted anatomical feature comprises any one a cheek region, a jaw region, a back of the head region, a region of an ear and any combination thereof.

15. A method of non-contact registration for an image guided surgical procedure, comprising:
    3-D scanning a region of interest (ROI) of a patient and a reference frame structure using a 3-D scanning device to capture a collection of spatial data points;
    constructing a digital mesh model from the collection of spatial data points, wherein the digital mesh model comprises:
    an ROI mesh model; and
    a reference frame mesh model;
    determining a location and a position of the reference frame mesh model within the digital mesh model;
    registering the reference frame mesh model with a registration reference frame model;

detecting an anatomical feature of the ROI mesh model and a corresponding anatomical feature of a patient registration model utilizing a facial detection algorithm;

weighting the anatomical feature of the ROI digital mesh model and the corresponding anatomical feature of the patient registration model utilizing the facial detection algorithm; and registering the ROI mesh model with the patient registration model utilizing the weighted anatomical feature of the ROI digital mesh model and the patient registration model;

wherein the weighting of the anatomical feature is based on a level of repeatability of a position of the anatomical feature relative to the ROI.

16. The method of claim 15, wherein the weighting of the anatomical feature is high when the position of the anatomical feature is highly repeatable relative to the ROI.

17. The method of claim 16, wherein the high weighted anatomical feature comprises any one of the bony contours around an eye, an eyebrow, a nose, a forehead region, and any combination thereof.

18. The method of claim 15, wherein the weighting of the anatomical feature is low when the position of the anatomical features is variable relative to the ROI.

19. The method of claim 18, wherein the low weighted anatomical feature is removed from the facial detection algorithm.

20. The method of claim 18, wherein in the low weighted anatomical feature comprises any one a cheek region, a jaw region, a back of the head region, a region of an ear and any combination thereof.

21. The method of claim 15, wherein the anatomical feature comprises any one of a nose, an eye, an ear, a mouth, a cheek, an eyebrow, a jaw, and any combination thereof.

22. The method of claim 15, further comprising creating the patient registration model from any one of computed tomography (CT), magnetic resonance image (MRI), computer tomography angiography (CTA), magnetic resonance angiography (MRA), and intraoperative CT images.

* * * * *

UNITED STATES PATENT AND TRADEMARK OFFICE
CERTIFICATE OF CORRECTION

| | | |
|---|---|---|
| PATENT NO. | : 12,033,295 B2 | Page 1 of 1 |
| APPLICATION NO. | : 17/654438 | |
| DATED | : July 9, 2024 | |
| INVENTOR(S) | : Ryan D. Datteri et al. | |

It is certified that error appears in the above-identified patent and that said Letters Patent is hereby corrected as shown below:

On the Title Page

Column 1, Other Publications, Line 2, Delete "Interative" and insert --Iterative-- therefor In the Specification Column 7, Detailed Description, Line 48, Delete "150 $a$" and insert --150$a$-- therefor Column 7, Detailed Description, Lines 50-51, Delete "151 $a$," and insert --151$a$,-- therefor Column 7, Detailed Description, Line 51, Delete "152 $a$," and insert --152$a$,-- therefor Column 7, Detailed Description, Line 51, Delete "153 $a$." and insert --153$a$.-- therefor Column 7, Detailed Description, Line 56, Delete "150 $b$" and insert --150$b$-- therefor Column 7, Detailed Description, Line 59, Delete "151 $b$," and insert --151$b$,-- therefor Column 7, Detailed Description, Line 59, Delete "152 $b$," and insert --152$b$,-- therefor Column 7, Detailed Description, Line 59, Delete "153 $b$." and insert --153$b$.-- therefor Column 7, Detailed Description, Line 61, Delete "150 $b$," and insert --150$b$,-- therefor Column 7, Detailed Description, Line 64, Delete "150 $b$" and insert --150$b$-- therefor In the Claims Column 12, Line 5, In Claim 6, after "comprises:", insert --¶--

Signed and Sealed this
Twenty-second Day of April, 2025

Coke Morgan Stewart
*Acting Director of the United States Patent and Trademark Office*